United States Patent [19]

Spector

[11] 4,151,268

[45] Apr. 24, 1979

[54] BARBITURIC ACID ANTIGENS AND ANTIBODIES SPECIFIC THEREFOR

[75] Inventor: Sidney Spector, Livingston, N.J.

[73] Assignee: Hoffmann-La Roche Inc., Nutley, N.J.

[21] Appl. No.: 860,810

[22] Filed: Dec. 15, 1977

Related U.S. Application Data

[60] Division of Ser. No. 670,210, Mar. 23, 1976, Pat. No. 4,107,157, which is a continuation of Ser. No. 378,744, Jul. 12, 1973, abandoned, which is a division of Ser. No. 174,517, Aug. 24, 1971, Pat. No. 3,766,162.

[51] Int. Cl.$^2$ .............................................. G01N 33/16
[52] U.S. Cl. .......................................... 424/1; 424/12; 260/112 B
[58] Field of Search ............................. 424/1, 12, 18; 260/112 B

[56] References Cited

PUBLICATIONS

Usategui-Gomez et al., Clin. Chem., vol. 21, No. 10, Sep. 1975, pp. 1378–1382.
Spiehler et al., Clin. Chem., vol 22, No. 6, Jun. 1976, pp. 749–753.
Cleeland et al., Clin. Chem., vol. 26, No. 6, Jun. 1976, pp. 712–725.

*Primary Examiner*—Benjamin R. Padgett
*Assistant Examiner*—Christine M. Nucker
*Attorney, Agent, or Firm*—Jon S. Saxe; George M. Gould

[57] ABSTRACT

Barbituric acid antigens are prepared by coupling 5- or 5,5-substituted barbituric acid to immunogenic carrier materials. In preferred embodiments, proteins are used as the carrier materials and the coupling is effected by an amide linkage between the 5-substituent of the barbituric acid and a carboxyl or amino group of the protein. The resulting antigens produce immunological effects when injected into host animals, including the formation of antibodies specific for 5- and 5,5-substituted barbituric acids. These specific antibodies are useful in bioanalytical techniques for the assay of barbituric acids in biological fluids.

7 Claims, No Drawings

BARBITURIC ACID ANTIGENS AND ANTIBODIES SPECIFIC THEREFOR

This is a division, of application Ser. No. 670,210 filed Mar. 23, 1976, now U.S. Pat. No. 4,107,157 which is a continuation application of Ser. No. 378,744, filed July 12, 1973, now abandoned, which is a divisional application of Ser. No. 174,517, filed Aug. 24, 1971, now U.S. Pat. No. 3,766,162, issued Oct. 16, 1973.

BACKGROUND OF THE INVENTION

The large increase in the use of sedatives including barbituric acids by the general population has brought with it a substantial need to improve analytical techniques for the determination of such materials in biological fluids. In many instances, medical treatment centers are faced with the need of determining the identity of a sedative taken by a patient who, being in a comatose condition, is unable to supply such information to the treating physician. There has also been much publicity in recent years concerning drug abuse, particularly abuse of sedatives such as barbituric acid derivatives.

At present, procedures for the identification of barbituric acid derivatives involve extraction and thin layer chromatographic methods. These techniques have the disadvantage of being relatively time consuming, laborious and lacking great sensitivity. A more rapid and highly sensitive assay for the presence of barbituric acid derivatives in biological fluids would thus represent an extremely important advance in the art.

It has been known in the art for some time that various small molecules (haptens), which by themselves are wholly devoid of antigenicity, can modify the antigenic properties of a protein when a small molecule is combined with the protein through stable covalent linkages. In U.S. Pat. No. 2,372,066, patented Mar. 20, 1945, it is disclosed that antigens may be prepared by combining histamine or histamine-like compounds by linking the imidazole ring to a desired protein through a radical containing a group capable of coupling with the protein. These antigens are used either by direct injection into a subject whereby resistance, refractoriness or active immunity is developed in said subject or for injecting into host animals from which antibodies specific to the hapten moiety, e.g. the histamine or histamine-like substance are developed.

A similar contemporary disclosure was made by Landsteiner in the "Specificity of Serological Reactions", Harvard University Press, Cambridge, Mass. (1945) wherein p-amino benzene arsonic acid was coupled to a protein via its diazonium salt to form a chemically simple, well-defined compound which was antigenic and stimulated the production of antibodies. Furthermore, the antibodies to this immunogen (conjugated protein) can combine with the small molecule, e.g. the arsonic acid which is unattached to any protein. This antibody is quite specific in activity. For example, if an isomer of arsonilic acid, in which the $-AsO_3H$ group is in the meta position relative to the amino group, is utilized, it will not combine with the antibody formed against the protein-arsonilic acid complex in which the $-AsO_3H$ group is para to the amino group.

It should be mentioned that it is not yet possible, in the present state of the art, to predict or determine what properties are required to enable a molecule to act as an antigen. At one time, molecular weight and the possession of an aromatic group were thought to be the deciding factors. With time, the critical molecular weight required for antigenicity has been remarkably reduced. It is still believed, however, that the molecular weight will to some extent, determine the antigenic capabilities of a molecule. Other factors such as molecular shape and chemical reactivity must also play a role in the antigenic properties and thus render prediction of such properties exceedingly more difficult.

DETAILED DESCRIPTION OF THE INVENTION

The present invention relates to a novel class of antigens comprising a 5- or 5,5-substituted barbituric acid hapten moiety coupled to an immunogenic carrier material. In preferred embodiments, the barbituric acid derivative is covalently bonded to a protein or polypeptide molecule by a peptide linkage. This peptide linkage involves either a carboxyl group located on a 5-substituent of the barbituric acid moiety and an amino group on the protein or polypeptide chain or an amino group located on the 5-substituent of the barbituric acid moiety and a carboxyl group on the protein or polypeptide chain. Additionally, the present invention relates to antibodies which will complex with some specificity with the 5- or 5,5-substituted barbituric acid haptens. These antibodies are produced by treating host animals with the aforesaid antigen. Such specific antibodies are readily isolated from sera obtained from host animals after treatment of these host animals with the antigen.

As used herein, the term "immunogenic carrier material" is meant to include those materials which have the property of independently eliciting an immunogenic response in a host animal when injected therein and which can be coupled with covalent bonding to the aforedescribed barbituric acid hapten. Suitable carrier materials include, for example, proteins; natural or synthetic polymeric compounds such as polypeptides, e.g. polylysine or polyglutamic acid; polysaccharides; and the like. Particularly preferred carrier materials for the practice of the present invention are proteins and polypeptides, especially proteins.

The identity of the protein material utilized in the preparation of a preferred antigen of the present invention is not critical. Examples of preferred proteins useful in the practice of this invention include mammalian serum proteins such as, for example, human gamma globulin, human serum albumin, bovine serum albumin, rabbit serum albumin and bovine gamma globulin. Other suitable protein products will be suggested to one skilled in the art. It is generally preferred that proteins be utilized which are foreign to the animal hosts in which the resulting antigen will be employed.

The barbituric acid derivative useful to prepare the antigens of the present invention are those which are mono- or di-substituted in the 5-position and which contain no substituents on the nitrogen atoms in the 1- and 3-positions. There must also be present on the 5-substituent of the aforesaid barbituric acid at least one carboxy or amino group which serves to couple with the immunogenic carrier material. Examples of groups which may be present in the 5-position of a barbituric acid for the above purpose are straight or branched chain alkyl groups, e.g. methyl, ethyl, n-butyl, isobutyl, n-hexyl, isopropyl, sec.-butyl, 3-pentyl, α-methyl-butyl and α,γ-dimethyl-butyl; cycloalkyl groups, e.g. cyclopentyl and cyclohexyl; aryl groups, e.g. phenyl; alkenyl groups, e.g. allyl, methallyl and so forth; carboxy-substituted-straight or branched chain alkyl groups, e.g. carboxy-methyl, β-carboxy-ethyl, β-carboxy-α-methylethyl, $\beta$-carboxy-$\alpha,\beta,\beta$-trimethyl-ethyl, $\beta$-carboxy-$\beta$-ethyl-$\alpha$-methyl-ethyl, $\gamma$-carboxy-$\alpha$-methyl-propyl, $\alpha,\beta$-dicarboxy-ethyl, and so forth; carboxy-substituted cycloalkyl groups, e.g. 2-carboxy-cyclopentyl, 2-carboxycyclohexyl, and so forth; carboxy-substituted aralkyl groups, e.g. p-carboxy-benzyl, p-carboxy-$\alpha$-methylbenzyl and so forth. Barbituric acid derivatives having substituent groups containing an amino function in place of the carboxyl function may be prepared from those having a carboxyl function by a number of methods, for example, the Hoffmann reaction, the Curtius reaction, the Schmidt reaction and so forth. Barbituric acids having an amino substituent in the 5-side chain may also be prepared from the carboxy compound by reacting the carboxy compound with a derivative of a diamine such as para-phenylenediamine. In this case the carboxyl group is converted into an amide by linkage to one amino group of the diamine moiety. The other amino group, can then be utilized to form an amide linkage with the carboxyl group of a protein or polypeptide, as described below.

The coupling of the barbituric acid hapten with the protein to form the antigen of the present invention can be readily accomplished utilizing techniques now well known in protein chemistry for establishing peptide bonds. Thus, for example, one such technique would involve dissolving the protein and a dehydrating agent in a suitable inert solvent followed by adding a large molar excess of the desired barbituric acid hapten. The reaction may be conducted at a temperature in the range of from about 0° C. to about 50° C., although higher or lower temperatures might be employed depending on the nature of the reactants and the denaturization temperature of the protein. A most preferable temperature is from about 0° to about room temperature. It is desirable to utilize a slightly acidic reaction medium, e.g., a medium having a pH in the range of from about 3 to 6.5, most preferably in the range of from about 4 to 6.5. Upon completion of the reaction, the excess hapten molecules and dehydration agent may be removed by dialysis. The dialysis may be monitored by checking the dialysate for the presence of hapten or dehydrating agent or, alternatively, may be conducted for a pre-determined period of time, e.g., 3 days. Purified antigen is recovered as a residue in the dialysis bag.

The dehydrating agent which may be used in the aforesaid reaction will be selected from those commonly employed in peptide chemistry for initiating the formation of a peptide bond. A particularly suitable group of dehydrating agents comprise the carbodiimides, most preferably, dicyclohexylcarbodiimide or 1-ethyl-3-(3-dimethylaminopropyl)-carbodiimide. The amount of molar excess of the hapten over the protein in the aforesaid reaction will, of course, depend upon the identity of the hapten utilized and the protein selected for the reaction. Generally, a molar excess in the range of from about 100 to 1000, most preferably in the range of from about 500 to 1000 will be utilized. It is generally found that from about 2 to about 3 barbituric acid derivative groups are added to a molecule of protein depending of course on the amount of molar excess of hapten used.

Another useful technique for the preparation of the antigens of the present invention is to first form an activated derivative of the carboxyl group of the hapten moiety and then to react said activated derivative with the protein to form the desired antigen. Suitable activated derivatives include activated esters such as p-nitrophenyl esters; acylimidazoles; and so forth. Activated ester derivatives are conveniently prepared from the free acid by reacting said free acid with the desired alcohol in the presence of a suitable dehydrating agent such as a carbodiimide, under reaction conditions similar to those described above. Acylimidazoles may be prepared by reacting the free carboxyl group with, for example, carbonyldiimidazole.

The antigen may be prepared from the activated derivative by contacting said activated derivative with the desired protein. As above, the antigen is usually purified by dialysis.

Antigens of the present invention may also be prepared by coupling barbituric acid haptens having a free amino group with the carboxyl group of a protein. The technique involved here is identical to that described above except that activated derivatives of the free carboxyl groups of the protein would be prepared and then reacted with the amine containing hapten.

The antigens of the present invention can also be prepared from polypeptides having free carboxyl or amino groups in the same manner as described above for proteins, using the carbodiimide dehydration technique. Suitable polypeptides containing free carboxyl groups include poly-L-glutamic acid. Suitable polypeptides containing free amino groups include poly-L-lysine.

Another useful technique for preparing antigens from polypeptide carrier materials is to first react a barbituric acid hapten containing a free amino group with a poly ester of a polypeptide containing side chain carboxyl group, e.g., poly-$\gamma$-benzyl-L-glutamate, according to known procedures, to form the new polypeptide bond. By employing this technique, a high ratio of hapten to carrier material can be effected. Thus, if poly-$\gamma$-benzyl-L-glutamate is utilized, one molecule of amino hapten can be introduced for each amino acid in the polypeptide chain, providing a large number of active sites to induce antibody formation. The number of active sites can be varied, if desired, by using a carrier material which is a copolymer of an amino acid containing a side chain carboxyl group with another amino acid not having a carboxyl side chain, e.g., a copolymer of glutamic acid and lysine. In such a copolymer, the ratio of, for example, the glutamic acid to the lysine, can be controlled as desired.

The antigen of the present invention may be utilized to induce formation of antibodies specific to 5- and 5,5-substituted barbituric acids in the serum of host animals by injecting the antigen in such host repeatedly over a period of time, collecting the serum, precipitating the antibody with a neutral salt solution and purifying the antibody by dialysis and column chromatography. Suitable host animals for this purpose include mammals such as rabbits, horses, goats, guinea pigs, rats, cows, sheep, etc. The resulting antibody will have a multiplicity of active sites which will selectively complex with either the substituted barbituric acid or the anitgen prepared therefrom, as described above.

The formation of substituted barbituric acid specific antibodies in the host animals may be monitored by taking blood samples from the host animals and adding to it an amount of the barbituric acid-protein antigen. The presence of a precipitate indicates antibody activity. The antigen treatment of the animal can be continued until the antibody titer reaches the desired level of activity. For the purposes of this application, the antibody titer is defined as being the maximum concentration of protein precipitated following the addition of varying known concentrations of antigen to fixed volumes of serum, e.g., 0.5 ml.

The barbituric acid specific antibodies can be isolated from the sera of treated host animals by utilizing techniques well known in the biochemical arts. For example, the sera obtained from treated host animals can be acted upon by a neutral salt which will effect precipitation of the desired barbituric acid specific antibodies. Suitable neutral salts for this purpose include sodium sulfate, magnesium sulfate, a sodium hydrogen phosphate mixture or ammonium sulfate. The neutral salt preferred for the purpose of the present invention is ammonium sulfate. Purification techniques subsequent to the precipitation step may also be employed. For example, the obtained antibodies may be further purified by subjecting such antibody to dialysis and column chromatography. The resulting antibody may be characterized as being a gamma globulin having a molecular weight of about 160,000. This antibody will complex with barbituric acid haptens and barbituric acid antigens described above.

The specific antibodies of the present invention are useful as reagents in biochemical assays for the determination of the presence of 5- and 5,5-substituted barbituric acid derivatives in biological fluids. A particularly preferred assay procedure is an immuno precipitation procedure which can be used to measure nanogram amounts of barbituric acid derivatives in serum or urine. In such a procedure, a known amount of labelled barbituric acid derivative is mixed with the barbituric acid specific antibody and a sample containing the unknown quantity of barbituric acid derivative. The amount of barbituric acid derivative in the sample can be determined by measuring the amount of competitive inhibition observed between the binding of the labeled barbituric acid derivative and the sample barbituric acid derivative with the barbituric acid specific antibody and then calculating the amount of barbituric acid derivative in the sample from a standard curve. Suitable labeled barbituric acid derivatives for this purpose include isotopically labeled barbituric acid derivatives, particularly those labeled with carbon 14, as well as barbituric acid derivatives labeled with an electron spin resonance group. Examples of the use of various electron spin resonance labeled molecules in bioassays are to be found in U.S. Pat. Nos. 3,453,288, 3,481,952 and 3,507,876.

The antibodies prepared according to the present invention are specific for haptens and antigens in which the basic barbituric acid ring is mono- or di-substituted in the 5-position. Examples of such barbituric acids include barbital, pentobarbital and phenobarbital. The antibody will not differentiate between barbituric acids having different substituents in the 5-position. If the basic barbituric acid ring system contains one or more substituents on the nitrogen atoms in the 1- and 3-positions, the binding of such haptens or the antigens derived therefrom to the antibody is greatly decreased so that such barbituric acid derivatives can be readily distinguished from those described above by running the assay at a dilution at which little or no binding occurs. If the basic barbituric acid ring system is changed, for example, by changing the ring size, no binding to the antibody is observed. Thus, it can be seen that the technique of the present invention allows for determination of minute amounts of 5- and 5,5-substituted barbituric acid derivatives with great specificity.

The novel antigens and antibodies of the present invention may be utilized in conjunction with conventional additives, buffers, stabilizers, diluents, or in combination with other physiologically active substances. The preparation and use of compositions containing antigens or antibodies in conjunction with physiologically acceptable adjuvants is now well known in the art.

This invention is further illustrated by the following specific examples.

EXAMPLE 1

Preparation of antigen 5-($\beta$-Carboethoxy-$\alpha$-methyl-ethyl)-barbituric acid was treated with allyl bromide at 50° C. to afford 5-allyl-5-($\beta$-carboethoxy-$\alpha$-methyl-ethyl)-barbituric acid, m.p. 114°. Alkaline saponification of this compound afforded 5-allyl-5-($\beta$-carboxy-$\alpha$-methyl-ethyl)-barbituric acid, which was recrystallized from water, m.p. 200°.

Anal. Calcd. for $C_{10}H_{14}N_2O_5$: C, 51.96; H, 5.55. Found: C, 52.10; H, 5.32.

5-Allyl-5-($\beta$-carboxy-$\alpha$-methyl-ethyl)-barbituric acid (10 mg.) was dissolved in 0.5 ml. dimethyl formamide (DMF) and was treated first with a solution of 5 mg. dicyclohexyl carbodiimide (DCC) in 0.5 ml. DMF and then with a solution of 12 mg. p-nitrophenol in 0.5 ml. DMF at 4° C. After standing overnight at this temperature, the mixture was evaporated to dryness and then dissolved in 1.5 ml. of a 1:1 mixture of glycerine-water. Bovine serum albumin (20 mg.) was added and the mixture was allowed to react for eight hours at room temperature and then overnight at 4° C. The product was then dialyzed against distilled water for two days to remove unreacted barbituric acid derivative and the p-nitrophenol which was displaced from the barbituric acid by the protein, to afford the bovine serum albumin-barbituric acid conjugate. The degree of substitution was estimated to be 2–3 moles of barbiturates per mole of protein, calculated from the extinction coefficient of the absorbtion at 202 m$\mu$.

In a similar experiment, an antigen was prepared in the identical manner using bovine gamma globulin as the protein.

EXAMPLE 2

Preparation of antibody

New Zealand albino rabbits were immunized with 1 mg. of barbituric acid-bovine gamma globulin antigen prepared as described in Example 1. 100 $\mu$g. of the conjugate in phosphate-buffered saline pH 7.2 was emulsified with an equal volume of complete Freund's adjuvant. The initial dose was 1.6 ml., 0.4 ml. being injected into each foot pad. A booster injection of 100 $\mu$g. of antigen in adjuvant was given every six to eight weeks, 25 $\mu$g. in each of the foot pads. Blood was collected five to seven days after booster injections and the serum containing the antibody was separated by centrifugation.

EXAMPLE 3

Radioimmunoassay

The radioimmunoassay was performed by incubating various dilutions of antisera obtained in Example 2 in the presence of $8 \times 10^{-4}$ $\mu$c [$C^{14}$] pentobarbital sodium (New England Nuclear, 4.13 mc/mM), approximately 1,000 counts/minute, at 4° C.; overnight. After incubation, a neutral saturated ammonium sulfate solution (volume equal to incubation medium) was added to all tubes. The precipitate, containing antibody-bound pentobarbital, was washed two times with an equal volume of 50% saturated ammonium sulfate and then dissolved in 0.5 ml. of commercial detergent solubilizer such as "NCS solubilizer" and quantitatively transferred and counted in a Packard Tri-Carb liquid scintillation spectrometer. The tube which contains radioactive pentobarbital and antiserum but no unlabeled pentobarbital serves as a measure of maximum antibody-bound radioactivity. The addition of increasing amounts of unlabeled pentobarbital to a fixed amount of labeled pentobarbital and antiserum resulted in a competitive inhibition of the labeled pentobarbital for the formation of the antibody-hapten complex. The data obtained is summarized below in Table I.

Table I

| Nanograms non-radioactive pentobarbital added | Percent inhibition of binding of pentobarbital-$C^{14}$ |
|---|---|
| 1 | 10 |
| 5 | 20 |
| 10 | 28 |
| 20 | 43 |
| 30 | 52 |
| 40 | 63 |

The above data clearly demonstrates the sensitivity of the method. When plotted in graphic form, the data contained in the above table demonstrates a linear relationship between the amount of non-radioactive pentobarbital added and the percent of inhibition found. The addition of 5 nanograms of pentobarbital in the sample volume of 10 µl. caused a 20% inhibition of binding of the labeled compound. Greater sensitivity is possible by employing larger sample volumes.

Comparison runs were also carried out with other barbituric acid derivatives and compounds resembling barbituric acid somewhat in structure. The antibody was capable of recognizing barbital, pentobarbital and phenobarbital, all of which differ only by the substituents on $C_5$. In contrast, the antibody failed to bind hexobarbital or thiopental at similar concentrations. These compounds have a 1-methyl and 2-thio substituents, respectively.

I claim:

1. A method for the assay of a 5-substituted-1,3-unsubstituted barbituric acid derivative in a sample which method comprises:

adding said sample to a solution containing a known amount of a labeled 5-substituted-1,3-unsubstituted-barbituric acid derivative and an antibody specific for 5-substituted-1,3-unsubstituted-barbituric acid derivatives consisting of a gamma globulin fraction protein having a multiplicity of sites which will selectively complex with said 5-substituted-1,3-unsubstituted-barbituric acid derivative, measuring the percent inhibition of binding of said labeled 5-substituted-1,3-unsubstituted-barbituric acid derivative, and determining the amount of 5-substituted-1,3-unsubstituted-barbituric acid derivative present in said sample by comparing said percent inhibition value to a standard curve obtained by adding known amounts of said 5-substituted-1,3-unsubstituted-barbituric acid derivatives to a fixed mixture of said labeled 5-substituted-1,3-unsubstituted barbituric acid derivative and said antibody and determining the percent inhibition of binding for each known amount of said 5-substituted-1,3-unsubstituted-barbituric acid derivative.

2. The method of claim 1 wherein said assay method is radioimmunoassay.

3. The method of claim 2 wherein said labeled 5-substituted-1,3-unsubstituted-barbituric acid derivative is selected from the group consisting of pentobarbital-$C^{14}$, phenobarbital-$C^{14}$ and barbital-$C^{14}$.

4. The method of claim 2 wherein said 5-substituted-1,3-unsubstituted-barbituric acid derivative in said sample is pentobarbital.

5. The method of claim 2 wherein said 5-substituted-1,3-unsubstituted-barbituric acid derivative in said sample is phenobarbital.

6. The method of claim 2 wherein said 5-substituted-1,3-unsubstituted-barbituric acid derivative in said sample is barbital.

7. The method of claim 2 wherein the measuring of the percent inhibition of binding of said labeled 5-substituted-1,3-unsubstituted-barbituric acid is done by means of liquid scintillation counting.

* * * * *